United States Patent [19]

Currie et al.

[11] Patent Number: 4,612,301
[45] Date of Patent: Sep. 16, 1986

[54] METAL COORDINATION COMPLEXES OF HETEROPOLYACIDS AS CATALYSTS FOR ALCOHOL CONVERSION

[75] Inventors: Janie K. Currie, Russell; Arthur J. Cooper, Garfield Heights; Frederick A. Pesa, Aurora, all of Ohio

[73] Assignee: The Standard Oil Company, Cleveland, Ohio

[21] Appl. No.: 724,139

[22] Filed: Apr. 17, 1985

[51] Int. Cl.$^4$ ............ B01J 31/14; B01J 31/12
[52] U.S. Cl. .................. 502/154; 502/162; 502/164; 502/165; 502/167; 502/209; 502/210; 502/211; 585/639; 585/640
[58] Field of Search ............ 502/154, 162, 164, 165, 502/167, 209, 210, 211

[56] References Cited

U.S. PATENT DOCUMENTS

| | | | |
|---|---|---|---|
| 3,485,877 | 12/1969 | Hargis et al. | 502/211 X |
| 4,182,745 | 1/1980 | Nishida et al. | 502/209 X |
| 4,205,182 | 5/1980 | Izumi et al. | 502/210 X |
| 4,419,270 | 12/1983 | Ueshima et al. | 502/209 |

FOREIGN PATENT DOCUMENTS

| | | |
|---|---|---|
| 59722 | 5/1981 | Japan . |
| 123946 | 9/1981 | Japan . |

OTHER PUBLICATIONS

Chem. Ab., vol. 69, 37050s (1968).
Bull. Chem. Soc. Jpn., 55, pp. 2555–2559 (1982).
J. of Catalysis, vol. 77, pp. 473–484 (1982).
J. of Catalysis, vol. 81, pp. 61–66 (1983).
Ono et al, "Conversion of Methanol—", Pan-Pacific Synfuels Conference, vol. I, Nov. 1982.
Williams et al, "Organic Pigments", Ind. and Eng. Chem., pp. 1507–1510, Aug. 1955.
Chem. Ab., vol. 55, 25159d.
Misono et al, Bull. Chem. Soc. Jpn., vol. 55, No. 2, pp. 400–406 (1982).
Tomioka et al, Tetrahedron Letters, vol. 23, No. 5, pp. 539–542 (1982).
Klinkenberg et al, Petroleum, p. 393(e) (1963).
Ono et al, J.C.S. Chem. Comm., pp. 400–401 (1981).

*Primary Examiner*—Patrick P. Garvin
*Attorney, Agent, or Firm*—Charles S. Lynch; John E. Miller; Larry W. Evans

[57] ABSTRACT

A new catalyst system for the conversion of short-chain aliphatic alcohols to hydrocarbons having the formula

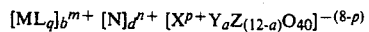

$$[ML_q]_b{}^{m+} [N]_d{}^{n+} [X^p + Y_a Z_{(12-a)} O_{40}]^{-(8-p)}$$

wherein:
[ML] is an organometallic compound where M is at least one metal selected from Group IIIA, IVA, VA, IB, IIB, IVB, VB, VIA, Fe, Co, and Ni; and L is an organic ligand,
N is a positively charged species including a positively charged organic ligand,
X is at least one element selected from P, Si, As, Ti, Zr, B, Co, Cu or Sn,
Y and Z are independently selected from W, Mo, or V,
m+n=8-p
q=1-6
0<a≦12
0≦d<3
b=1 to 3.

4 Claims, No Drawings

METAL COORDINATION COMPLEXES OF HETEROPOLYACIDS AS CATALYSTS FOR ALCOHOL CONVERSION

BACKGROUND OF THE INVENTION

The present invention relates to a new catalyst system and a process for using this catalyst for the conversion of short chained alcohols such as methanol to hydrocarbons. In particular, the present invention is directed to a new catalyst system used in a process of converting methanol to lower unsaturated hydrocarbons in the $C_2$–$C_4$ range.

The catalytic conversion of methanol to hydrocarbons is a well-known process. Many different catalysts have been described in the literature as effective in this process. For example, zeolite-based catalysts, metal sulfates, metal phosphates, and heteropolyacids have been shown as catalytic in the conversion of methanol to hydrocarbons.

Industrial commitment to methanol conversion or upgrading is increasing for a number of reasons. In recent years, heteropolyacids have been attracting attention since they show activity even at temperatures as low as 300° C. because of their strong acidity. In Japanese Patent Application No. 1980, 121,018, published Mar. 17, 1982 as 1982-46925, heteropolyacids are disclosed as being suitable for the conversion of short chained alcohols or oxygen containing compounds to hydrocarbons. The conditions for the reaction are from a temperature range of 250°–400° C. at a pressure of between ambient to 200 kg/cm$^2$g, and in the LHSV range of 0.1-10 hours$^{-1}$.

The heteropolyacid described in this Japanese patent application includes many compounds which vary depending on the condensed coordination elements, the central elements and the condensation forms. The Japanese patent application specifically discloses that the hydrogen ions of the heteropolyacids may be exchanged with other cations such as alkali metals including lithium, sodium, potassium, etc., nickel, cobalt, copper, manganese, lanthanide, silver, cesium, etc., to form the stable heteropolyacid salt. The Japanese patent application discloses that these materials when applied to supports such as clay or zeolite, give improved conversion in the manufacture of the hydrocarbons.

Moreover, U.S. Pat. No. 3,485,877 discloses the use of organo metallic palladium or platinum heteropolyacid salt catalysts for converting ethylenically unsaturated hydrocarbons (e.g., ethylene) to carbonylic compounds (acetaldehyde).

Unfortunately, even the results achieved by the use of supported heteropolyacids/salts of the Japanese patent application leave much to be desired. Accordingly, there is still significant room for improvement in the use of heteropolyacids/salts for the conversion of methanol to short-chained hydrocarbons. The present invention is directed to an improvement in the catalyst system used and the process for conversion of methanol to the short-chained hydrocarbons, and in particular, unsaturated short-chained hydrocarbons such as ethylene, propylene and butylene.

SUMMARY OF THE INVENTION

It is the primary object of the present invention to provide a new catalyst system for use in conversion of short-chained aliphatic alcohols to hydrocarbons.

It is a further object of the present invention to provide a new catalyst for a process for the conversion of methanol to hydrocarbons.

It is still another object of the present invention to provide a process for the conversion of methanol to short-chained hydrocarbons in the range of $C_1$ to $C_7$ by using a heteropolyacid salt.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the novel catalyst system of the present invention comprises a heteropolyacid salt having the following formula:

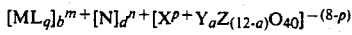

wherein:
[ML] is an organometallic compound where M is at least one metal selected from Group IIIA, IVA, VA, IB, IIB, IVB, VB, VIA, Fe, Co, and Ni; and L is an organic ligand,
N is a positively charged species including a positively charged organic ligand,
X is at least one element selected from P, Si, As, Ti, Zr, B, Co, Cu or Sn,
Y and Z are independently selected from W, Mo, or V,
m+n=8-p
q=1–6
0<a≦12
0≦d<3
b=1 to 3.

In a further aspect of the present invention, a process for the conversion of aliphatic oxygen containing organic compounds to hydrocarbons comprises passing an aliphatic oxygen containing organic compound at an elevated temperature for a time sufficient to produce the hydrocarbons over a catalyst having the formula:

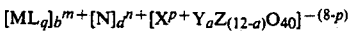

wherein:
[ML] is an organometallic compound where M is at least one metal selected from Group IIIA, IVA, VA, IB, IIB, IVB, VB, VIA, Fe, Co, and Ni; and L is an organic ligand,
N is a positively charged species including a positively charged organic ligand,
X is at least one element selected from P, Si, As, Ti, Zr, B, Co, Cu or Sn,
Y and Z are independently selected from W, Mo, or V,
m+n=8-p
q=1–6
0<a≦12
0≦d<3
b=1 to 3
and recovering the hydrocarbons.

The catalyst of the present invention offers significant advantages over the catalyst described in the previous procedures. The catalyst of the present invention offers greater flexibility in design because catalyst selectivity can be altered as desired by the use of appropriate ligands on the organometallic cation. The present invention offers greater ease of preparation than the zeolites used in the procedures described previously. The heteropolyacids are rapidly precipitated from solutions by the complex cations thereby avoiding prolonged hydrothermal crystallization which is characteristic of zeolite manufacture.

DETAILED DESCRIPTION OF THE INVENTION

Catalysts

The catalyst of the present invention are organometallic complexes of heteropolyacids. The catalyst can be used in the conversion of methanol to $C_1$ to $C_7$ hydrocarbons, in particular short chained unsaturated olefins such as ethylene and propylene.

The organometallic heteropolyacid catalyst complexes of the present invention have the formula:

$$[ML_q]_b{}^{m+}[N]_d{}^{n+}[X^{p+}Y_aZ_{(12-a)}O_{40}]^{-(8-p)}$$

wherein:
  [ML] is an organometallic compound where M is at least one metal selected from Group IIIA, IVA, VA, IB, IIB, IVB, VB, VIA, Fe, Co, and Ni; and L is an organic ligand,
  N is a positively charged species including a positively charged organic ligand,
  X is at least one element selected from P, Si, As, Ti, Zr, B, Co, Cu or Sn,
  Y and Z are independently selected from W, Mo, or V,
  m+n=8-p
  q=1-6
  O<a≦12
  O≦d<3
  b=1 to 3.

The structures of the heteropolyacids of these complexes (i.e., salts) are difficult to determine owing to the very complex nature and arrangement of the molecules. However, in general, heteropolyacids may best be described as complex inorganic substances of relatively high molecular weight in which two or more different cations or oxides of metals or metalloids are associated with varying, frequently indeterminate amounts of combined water as water of hydration. Typically, the phosphorus atom in phosphoheteropolyacids, the silicon atom in silicoheteropolyacids, etc., is regarded as the central atom of the molecule. This central atom is attached to 4 to 6 oxygen atoms. Outer $MoO_6$ or $WO_6$ octahedra are directly attached to the central atom through shared oxygen atoms. Thus, phosphomolybdic acid, phosphotungstic acid, phosphovanadic acid and the like can be formed. The heteropolyacids form a well known class of compounds and include, for example, phosphomolybdic acid, silicomolybdovanadic acid, titanomolybdotungstic acid, silicomolybdic acid, chromiomolybdic acid, stannotungstic acid, phosphotungstic acid, cobalt phosphomolybdate and the like. Most preferably, the heteropolyacids of the present invention are phosphotungstic or silicotungstic acid.

In a preferred embodiment of the present invention, M is selected from B, Cr, Fe and Ag. Most preferably, M is selected from B and Fe.

L may be any suitable organic ligand, illustrative of such materials are those described in Huheey, *Inorganic Chemistry* 1978, Chapter 13, herein incorporated by references. Typically, L may include $C_5H_5{}^-$, $C_5H_5CH_2N^+(CH_3)_3I^-$, and $C_6H_5N^+H_3$.

N may be any suitable positive charge species such as $Na^+$, $Li^+$, $Cs^+$, $Ag^+$, $NH_4{}^+$, $Cu^{+2}$, $Mn^{+2}$, etc.

In a preferred embodiment of the present invention, [ML] is selected from the group comprising aminoborate, ferrocene ammonium compounds, Cr-aniline, iron triazine and silver benzylamine or mixtures thereof.

The catalyst of the present invention can be used either in unsupported form or supported on suitable conventional carriers as $SiO_2$, $Al_2O_3$, Zeolite, etc. However, supported catalysts are preferred because of their superior selectivity and conversion to hydrocarbons.

The organometallic heteropolyacid complex catalyst of the present invention can be prepared by conventional procedures obvious to those skilled in the art. For example, the unsupported catalyst may be prepared by precipitation of the heteropolyanion from solution by the addition of a solution containing the organometallic cation. Supported catalyst may be prepared by impregnating the support (e.g. $SiO_2$—$Al_2O_3$) with a solution of cation followed by a second impregnation with a solution of the anion. This procedure results in the deposition of the organometallic complex on the surface of the support. Of course, if the organometallic complex is soluble in the solution, the solution may be used to impregnate the support.

Process Conditions

The process of the present invention is directed to the conversion of aliphatic oxygen containing organic compounds to hydrocarbons. In particular, the process of the present invention is directed to the conversion of short-chain aliphatic alcohols to $C_1+C_7$ hydrocarbons. More particularly, the process of the present invention is directed to the conversion of methanol to unsaturated hydrocarbons such as ethylene propylene.

While methanol is the preferred feed vapor for the process of the present invention, it should be understood that other feeds such as dimethylether and methylal (dimethoxymethane) can also be utilized.

The process of the present invention comprises contacting a vaporous stream of methanol at an elevated temperature with a catalyst having the formula:

$$[ML_q]_b{}^{m+}[N]_d{}^{n+}[X^{p+}Y_aZ_{(12-a)}O_{40}]^{-(8-p)}$$

wherein:
  [ML] is an organometallic compound where M is at least one metal selected from Group IIIA, IVA, VA, IB, IIB, IVB, VB, VIA, Fe, Co, and Ni; and L is an organic ligand,
  N is a positively charged species including a positively charged organic ligand,
  X is at least one element selected from P, Si, As, Ti, Zr, B, Co, Cu or Sn,
  Y and Z are independently selected from W, Mo, or V,
  m+n=8-p
  q=1-6
  O<a≦12
  O≦d<3
  b=1 to 3.
for a time sufficient to convert said methanol to a mixture of hydrocarbons and recovering said hydrocarbons.

Typically, the process is carried out at a temperature between about 200°–400° C. Most preferably, the temperature is between 275°–325° C.

The process is normally carried out at atmospheric pressure. However, elevated pressures may be utilized in the practice of the invention, for example, 5 atmospheres.

The contact time for the reaction ranges from 1 second to 20 hours. Preferably, the contact time is under 5 minutes.

Typically, the flow rate of the liquid feed into the reactor is between 1 to 10 ml/hr. Preferably, the flow rate is between 1 to 5 ml/hr.

In a preferred embodiment of the process of the present invention, the catalyst is placed in the reactor and pretreated by heating to an elevated temperature under an inert atmosphere prior to introduction of the methanol vapors. Most preferably, the pretreatment is at a temperature of about 325°–375° C. for about 2–4 hours.

For purposes of illustration, Table I below summarizes the results obtained in methanol conversion using phosphotungstic acid (PTA) catalyst on an $SiO_2$—$Al_2O_3$ support.

The following specific examples are set forth to further illustrate and define the present invention.

The key feature of the data analysis set forth in the examples below is that selectivity for a given hydrocarbon product is based on carbon number. This is a more accurate reflection of the amount of $CH_3OH$ that is converted to a given product. Carbon balance is derived from a comparison of total moles of carbon found in the effluent, including unreacted MeOH, vs moles carbon (MeOH) in the feed. Carbon conversion compares the total moles of product carbon detected by Gas Chromatograph vs moles of feed MeOH. This number expresses % conversion to "useful" products, as it does not include any coke.

EXAMPLE I

Catalyst Preparation 1.00 g of $H_3PW_{12}O_{40}.24H_2O$ was dissolved in $\frac{1}{2}$ ml $H_2O$, 0.0237 g of $N(CH_2CH_2O)_3B$ (TEAB), was dissolved in $\frac{1}{4}$ ml $H_2O$. The solutions were mixed, affording a white precipitate.

$\frac{3}{4}$ ml $H_2O$ was added, then 10 drops of acetone which caused the precipitate to dissolve. 11.7 g of SA5205 (Norton $SiO_2$—$Al_2O_3$ Support) was impregnated with this solution in four portions. The catalyst was dried 30 minutes at 110° C.

Process

Reaction with methanol was carried out in a 5 cc reactor at 325° C. using 6.54 g of catalyst. Methanol was fed into the system at 1.04 ml/hr.

With 1.03 ml/hr MeOH, 29.3 cc/min. He, 301° C. reactor temperature, a gas chromatograph (GC) injection was made after a total of about 4 ml MeOH had passed over the catalyst.

Table II, below, summarizes the results for several runs made with this type of catalyst. The runs had different catalyst loading, run temperature and thermal pretreatment (350° C.-20 hours). As can be seen the best selectivity was obtained for the calcined product at 324° C. Comparison with the results of Table I shows that the catalyst of Example I at 324° C. had $C_2=$ and $C_3=$ selectivity of 17% with DME compared with approximately 6% with DME for PTA (phosphotungstic acid).

TABLE I

| | MeOH CONVERSION - CONTROL | | | |
|---|---|---|---|---|
| | Catalyst 8 wt % PTA on SA5205 | | | |
| | Temp. = 300° C. | | Temp. = 323° C. | |
| Product Selectivity | DME | Without DME | DME | Without DME |
| CO | — | — | .04 | .23 |
| $CO_2$ | .04 | — | .09 | .52 |
| $CH_4$ | .69 | 9.8 | 2.6 | 15.1 |
| $C_2=$ | 1.14 | 16.0 | 1.76 | 10.2 |
| $C_2$ | .03 | 0.5 | 0.43 | 2.5 |
| $C_3=$ | 1.92 | 27.0 | 4.15 | 24.1 |
| $C_3$ | .94 | 13.1 | 0.93 | 5.4 |
| $C_4=$ | .58 | 8.13 | 1.35 | 7.85 |
| $C_4$ | 1.78 | 24.9 | 2.06 | 12.7 |
| $C_5=$ | — | — | 1.54 | 9.5 |
| $C_5$ | — | — | 1.25 | 7.27 |
| $C_6=$ | — | — | — | — |
| $C_6$ | — | — | — | — |
| DME | 92.9 | 0 | 83.8 | 0 |
| CONVERSION | 90 | | 85 | |
| % UNSATURATES | 51 | | 54 | |

CT = 4.7–4.5 sec.
MeOH FEED = 26.2 mole % in He
SA5205 - Norton $SiO_2$—$Al_2O_3$ support

TABLE II

| | MeOH CONVERSION OVER COMPLEXES OF B—[$OCH_2CH_2$]$_3$N WITH PTA | | | | | |
|---|---|---|---|---|---|---|
| | Catalyst | | | | | |
| Product Selectivity | 1:1 B/PTA 8 wt % | 8 wt % 1:1 B/PTA Calcined | 8 wt % 1:1 B/PTA Calcined | | 1:1 B/PTA 20 wt % | 1:1 B/PTA 20 wt % |
| CO | — | 0.05 | 0.59 | (1.05) | 0.21 | 0.37 |
| $CO_2$ | — | 0.04 | 0.13 | (0.23) | 0.04 | 0.05 |
| $CH_4$ | 0.91 | 0.88 | 2.94 | (5.32) | 0.69 | 1.67 |
| $C_2=$ | 3.28 | 5.57 | 7.67 | (13.86) | 3.46 | 3.79 |
| $C_2$ | — | — | 0.41 | (0.74) | — | 0.16 |
| $C_3=$ | 6.03 | 5.78 | 8.77 | (15.83) | 3.45 | 4.58 |
| $C_3$ | 3.82 | 4.1 | 5.5 | (9.93) | 2.53 | 1.97 |
| $C_4=$ | 1.66 | 1.98 | 2.71 | (6.4) | 1.23 | 1.41 |
| $C_4$ | 9.75 | 17.1 | 18.2 | (31.4) | 10.15 | 6.76 |
| $C_5=$ | 5.58 | 8.27 | 8.44 | (15.25) | 4.98 | 2.85 |
| $C_5$ | — | — | 0.66 | (—) | 4.92 | 0.29 |
| DME | 68.9 | 56.3 | 43.9 | 0 | 68.4 | 76.1 |
| CONVERSION | | | | | | |
| % UNSATURATES | 53.3 | 49.4 | 49.2 | | 41.4 | 52.9 |
| TEMPERATURE | 301° C. | 300° C. | 324° C. | | 301° C. | 325° C. |

B = B($OCH_2CH_2$)$_3$N
CT ≈ 4.5 sec  MeOH = 26 mole % feed in He  Support = SA-5205
86% $Al_2O_3$α  11.8% $SiO_2$  low surface area
Numbers in parenthesis indicate calculation without DME

EXAMPLE II

Catalyst

Prep. of supported (ferrocene)-$CH_2N(CH_3)_3H_2PW_{12}O_{40}$ (FA/PTA) salt and reaction with MeOH at 325° C. 30 g of SA5205 (Norton $SiO_2$—$Al_2O_3$ support) in 10-20 mesh pieces was impregnated with 1.31 g of a 13 weight % solution of (ferrocene) $CH_2N(CH_3)_3I$ in methanol. A second impregnation with 3.53 g of a 74.5 weight % solution of $H_3PW_{12}O_{40}.24$ hydrate in water followed. The catalyst was dried in a vacuum for 6 hr. at room temperature. The mole ratio of complex cation to anion was 1:2.

Process 6.2 g of this catalyst was placed in a 5 cc reactor controlled at 325° C. Methanol was fed by a pump a 1.04 ml/hr, vaporized in the preheated zone and diluted by He gas at 29.11 cc/min. (26.2 mole % MeOH). The LHSV was 0.19 hr$^{-1}$ with contact time of 4.1 sec.

Tables II, IV and V set forth below contain the results of various runs performed with the FA/PTA complex made in accordance with the procedure of Example II.

TABLE III

MeOH CONVERSION OVER CpFeCpCH$_2$N(CH$_3$)$_3$/PTA ON SA5205
Cp = C$_5$H$_5$

| Product | Affect of Stoichiometry | | | | PTA/ SA5205 |
|---|---|---|---|---|---|
| | 1:10 | 1:3 | 1:2 | 1:1 | |
| CH$_4$ | 3.46 | 4.85 | 4.95 | 4.34 | 2.60 |
| C$_2$= | 4.11 | 4.50 | 5.31 | 1.29 | 1.76 |
| C$_2$ | 0.22 | 0.28 | 0.26 | — | 0.43 |
| C$_3$= | 5.53 | 5.48 | 8.44 | 1.93 | 4.15 |
| C$_3$ | 2.32 | 2.70 | 3.01 | 2.95 | 0.93 |
| C$_4$= | 1.32 | 1.00 | 1.64 | 0.86 | 1.35 |
| C$_4$ | 5.81 | 6.74 | 6.61 | — | 2.06 |
| C$_5$= | 1.63 | 1.57 | 1.82 | — | 1.54 |
| C$_5$ | 0.90 | 0.74 | 0.98 | — | 1.25 |
| DME | 74.7 | 72.1 | 67.0 | 88.5 | 83.8 |
| % CONVERSION | 72 | 52 | 77 | 27 | 80 |
| % UNSATURATES | 50 | 45 | 52 | 36 | 54 |

T = 325° C.
CT = 4 sec
25% MeOH Feed in He

TABLE IV

MeOH CONVERSION OVER Fe COMPLEXES OF PTA

Catalyst: CpFeCpCH$_2$N(Me)$_3$:PTA$^-$

| Product Selectivity | 1:2 | FeCl$_2$:PTA 1:2 | FeCl$_3$:PTA 1:2 |
|---|---|---|---|
| CO | — | — | — |
| CO$_2$ | — | — | — |
| CH$_4$ | 3.57 | 2.47 | 1.67 |
| C$_2$= | 5.00 | 1.86 | .94 |
| C$_2$ | .17 | — | — |
| C$_3$= | 6.37 | 3.10 | 1.55 |
| C$_3$ | 3.93 | — | .61 |
| C$_4$= | 1.67 | .90 | .41 |
| C$_4$ | 7.69 | .76 | .78 |
| C$_5$= | 2.19 | — | — |
| C$_5$ | — | — | — |
| C$_6$= | — | — | — |
| C$_6$ | — | — | — |
| C$_7$ | — | — | — |
| DME | 69.43 | 90.91 | 94.03 |
| CONVERSION | 52 | 84 | 83 |
| % UNSATURATES | 50 | 64 | 48 |
| CT = | 3 sec | 3 sec | 4 sec |

FeCl$_2$/PTA 8.7 wt % on SA5205  FeCl$_3$/PTA 8.3 wt % on SA5205
MeOH Feed = 26 mole % in He  FA/PTA 8.5 wt % on SA5205
Temperature = 322-325° C.

TABLE V

MeOH CONVERSION OVER PTA COMPLEXES WITH CpFeCpCH$_2$NMe$_3$ AND CpFeCpCH$_2$NMe$_2$

| Product Selectivity | Catalyst: CpFeCpCH$_2$N(Me)$_3$:PTA 1:2 | (Reverse) (Addition) 1:2 | Catalyst: CpFeCpCH$_2$N(Me)$_2$H:PTA 1:2 |
|---|---|---|---|
| CO | — | — | — |
| CO$_2$ | — | — | — |
| CH$_4$ | 3.57 | 4.04 | 4.65 |
| C$_2$= | 5.00 | 3.85 | 2.52 |
| C$_2$ | .17 | — | .17 |
| C$_3$= | 6.37 | 4.50 3.61 | |
| C$_3$ | 3.93 | 2.64 | 1.81 |
| C$_4$= | 1.67 | 1.10 | .63 |
| C$_4$ | 7.69 | 5.02 | 3.02 |
| C$_5$= | 2.19 | 9.75 | .60 |
| C$_5$ | — | — | — |

TABLE V-continued

MeOH CONVERSION OVER PTA COMPLEXES WITH CpFeCpCH$_2$NMe$_3$ AND CpFeCpCH$_2$NMe$_2$

| Product Selectivity | Catalyst—CpFeCp-CH$_2$N(Me)$_3$:PTA  1:2 | (Reverse) (Addition)  1:2 | Catalyst—CpFeCp-CH$_2$N(Me)$_2$H:PTA  1:2 |
| --- | --- | --- | --- |
| C$_6$= | — | — | — |
| C$_6$ | — | — | — |
| C$_7$ | — | — | — |
| DME | 69.43 | 69.11 | 82.98 |
| CONVERSION | 47 | 60 | 59 |
| % UNSATURATES | 50 | 62 | 43 |

CT = 4 sec    T = 325° C.
CATALYST COMPLEXES SUPPORTED 8.5 WT % ON SA-5205
MeOH FEED = 26 mole % in He Table III shows the results for complexes between PTA and the ferroceneammonium (CpFeCpCH$_2$N$^+$(CH$_3$)$_3$) cation ("FA") for various stoichiometries. The poor results for the 1:1 complex suggest that too much acid function has been lost. The 1:2 complex is better in terms of % unsaturation, C$_2$=-C$_3$= production and conversion to hydrocarbons past dimethylether. The synthesis and results were reproducible.

Table IV shows the results for the ferroceneammonium adduct (FA) of PTA vs simple Fe$^{+2}$ and Fe$^{+3}$ salts. As can be seen, the organometallic adduct is superior in the production of C$_2$ and C$_4$ unsaturates. This system was prepared by sequential impregnation on a support. The synthesis was repeated using reverse order of addition. Table V sets forth the results of the catalyst prepared by this sequence and shows very little change with the exception of increase in C$_5$=. Table V also shows that a similar adduct using a tertiary ferroceneamine (i.e., CpFeCpN(ME)H$_2$PTA) is not as active nor selective as the quaternary analogue.

EXAMPLE III

Palladium Complexes

Several syntheses were done in which the proportion of Pd(NH$_3$)$_4$$^{+2}$ to PTA was varied from 1:1 to 3:1. Elemental analysis found one composition, so that the actual reaction is believed to be 3[Pd(NH$_3$)$_4$]$^{+2}$Cl$_2$+2H$_3$PW$_{12}$P$_{40}$→[Pd(NH$_3$)$_4$]$_3$$^{+2}$[P-W$_{12}$O$_{40}$]$_2$$^{-3}$+6HCl. It is also possible that some of the NH$_3$ ligands were converted to NH$_4$$^+$Cl$^-$ leaving a simple Pd$^{+2}$HPW$_{12}$O$_{40}$$^{-2}$ salt. However, elemental analysis did not show a loss of N. To prepare a simple Pd/PTA salt for comparison, Pd(NO$_3$)$_2$ was reacted to give a 1:3 adduct. Test of these systems indicated that organometallic systems of this anion are not as good as PTA by itself.

EXAMPLE IV

The following example utilized a complex of more than one kind of metal and ligand. The catalyst were prepared according to the procedure set forth above in Example II. The mixed metal comprised a Ag-Fe complex. Table VI below summarizes the results obtained. Modification of the ferrocene ammonium cation with Ag shows an increase in hydrocarbons past DME but the ratio of olefins to hydrocarbons has decreased slightly. Modification with φ-CH$_2$N Me$_3$$^+$ shows a substantial increase in % hydrocarbon products. The desired increase in % olefins/hydrocarbons is not obtained.

TABLE VI

MeOH CONVERSION OVER MODIFIED Ag/PTA

| Cations | % Conversion | % Hydrocarbon Products | % Olefin/Products | % Olefin/H.C. |
| --- | --- | --- | --- | --- |
| Ag$_2$H | 90 | 73.3 | 30.9 | 42.1 |
| Ag$_{2.5}$FA$_{.5}$ | 80 | 85.3 | 29.9 | 35 |
| Ag$_{2.5}$BTMA$_{0.5}$ | 92 | 99.9 | 43.0 | 43 |

BTMA = C$_6$H$_5$—CH$_2$N(CH$_3$)$_3$

BENZYLTRIMETHYLAMMONIUM
FA = CpFeCp—CH$_2$N(CH$_3$)$_3$
T = 325° C.
LHSV = 0.2 HR$^{-1}$
CT = 4 sec
CATALYST FORM: NEAT PELLETS 10 MESH
% OLEFIN/PRODUCTS INCLUDES DME AS A PRODUCT
% OLEFIN/H.C. DOES NOT INCLUDE DME AS A PRODUCT The results of the present invention demonstrate the superiority of the organometallic complex catalyst of the present invention. The catalyst of the present invention demonstrate more selectivity to production of ethylene which is highly desirable. In addition, the organometallic complexes can be expected to offer greater flexibility because catalyst selectivity can be altered as desired by the use of the appropriate ligand and/or metal.

The foregoing description of the preferred embodiments of the invention has been presented for purposes of illustration and description. It is not intended to be exhaustive or to limit the invention to the precise form disclosed, and obviously many modifications and variations are possible in light of the above disclosure. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A heteropolyacid salt catalyst having the formula:

$$[ML_q]_b{}^{m+}[N]_d{}^{n+}[X^{p+}Y_aZ_{(12-a)}O_{40}]^{-(8-p)}$$

wherein:

[ML] is an organometallic compound where M is at least one metal selected from Group IIIA, IVA, VA, IB, IIB, IVB, VB, VIA, Fe, Co and Ni; and L is an organic ligand selected from aniline, triethanolamine, triazine, benzyltrimethylammonium, benzylamino, cyclopentadienyl, and trimethyl (cyclopentadienylmethylene)ammonium, N is selected from $Na^+$, $Li^+$, $Cs^+$, $Ag^+$, $NH_4{}^+$, $Cu^{+2}$ and $Mn^+$, X is at least one element selected from P, Si, As, T, Zr, B, Co, Cu or Sn, Y and Z are independently selected from W, Mo or V, m+n=8-p q=1-6 o<a≦12 o≦d<3 b=1 to 3.

2. The catalyst of claim 1 where said heteropolyacid salt is deposited on a support.

3. The catalyst of claim 2 wherein [ML] is selected from the group consisting of aminoborate, ferrocene, Cr-aniline, Fe-Triazine and Ag-Benzylamine.

4. The catalyst of claim 1 wherein M is selected from Fe and B.

* * * * *